US008945069B2

(12) United States Patent
Plumptre et al.

(10) Patent No.: US 8,945,069 B2
(45) Date of Patent: Feb. 3, 2015

(54) INJECTION DEVICE

(75) Inventors: David Plumptre, Droitwich Spa Worcestershire (GB); Christopher James Smith, Holmes Chapel (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 420 days.

(21) Appl. No.: 13/140,131

(22) PCT Filed: Dec. 18, 2009

(86) PCT No.: PCT/EP2009/067480
§ 371 (c)(1),
(2), (4) Date: Nov. 9, 2011

(87) PCT Pub. No.: WO2010/072662
PCT Pub. Date: Jul. 1, 2010

(65) Prior Publication Data
US 2012/0046643 A1 Feb. 23, 2012

(30) Foreign Application Priority Data
Dec. 23, 2008 (EP) ...................................... 08022317

(51) Int. Cl.
*A61M 5/00* (2006.01)
*A61M 5/315* (2006.01)

(52) U.S. Cl.
CPC ....... *A61M 5/31585* (2013.01); *A61M 5/31551* (2013.01); *A61M 5/3156* (2013.01); *A61M 5/31541* (2013.01); *A61M 5/31558* (2013.01);
(Continued)

(58) Field of Classification Search
USPC .......................................... 604/181, 211, 207
See application file for complete search history.

(56) References Cited

U.S. PATENT DOCUMENTS

| 4,475,905 A | 10/1984 | Himmelstrup |
| 5,599,314 A * | 2/1997 | Neill .............................. 604/207 |

(Continued)

FOREIGN PATENT DOCUMENTS

| EP | 1923084 | 5/2008 |
| WO | 96/39214 | 12/1996 |

(Continued)

OTHER PUBLICATIONS

International Search Report for International App. No. PCT/EP2009/067480, mailedFeb. 23, 2010.

*Primary Examiner* — Emily Schmidt
*Assistant Examiner* — Lauren M Peng
(74) *Attorney, Agent, or Firm* — McDonnell Boehnen Hulbert & Berghoff LLP

(57) ABSTRACT

An injection device (1) for administering a fixed dose of a medication is provided. The injection device (1) comprises a housing (2) wherein a drive mechanism comprising a drive member (3) is at least partially enclosed and a dosing element (34) which is fixed relative to the drive member (3). Here, a dose can be set by rotating the dosing element (34) relative to the housing (2) in a dose setting direction (s) and the dose can be dispensed by pushing the dosing element (34) towards the housing (2). Moreover, a method is provided for operating an injection device (1) for the administration of a fixed dose of a medication: A dose can be set by rotating a dosing element (34), a dose can be dispensed by pushing the dosing element (34) towards the housing (2) and a dose can be cancelled by rotating the dosing element (34) in a direction opposite to the dose setting direction (s).

26 Claims, 2 Drawing Sheets

(52) U.S. Cl.
CPC .. *A61M 2005/3152* (2013.01); *A61M 2205/581* (2013.01); *A61M 2205/582* (2013.01)
USPC ............................ 604/211; 604/181; 604/207

(56) References Cited

U.S. PATENT DOCUMENTS

| | | | |
|---|---|---|---|
| 6,235,004 B1 * | 5/2001 | Steenfeldt-Jensen et al. ............................ | 604/211 |
| 2008/0097322 A1 | 4/2008 | Markussen | |
| 2008/0221530 A1 * | 9/2008 | Glejbøl et al. ................ | 604/211 |

FOREIGN PATENT DOCUMENTS

| | | |
|---|---|---|
| WO | 01/10484 | 2/2001 |
| WO | 20041078239 | 9/2004 |
| WO | 20061079481 | 8/2006 |

\* cited by examiner

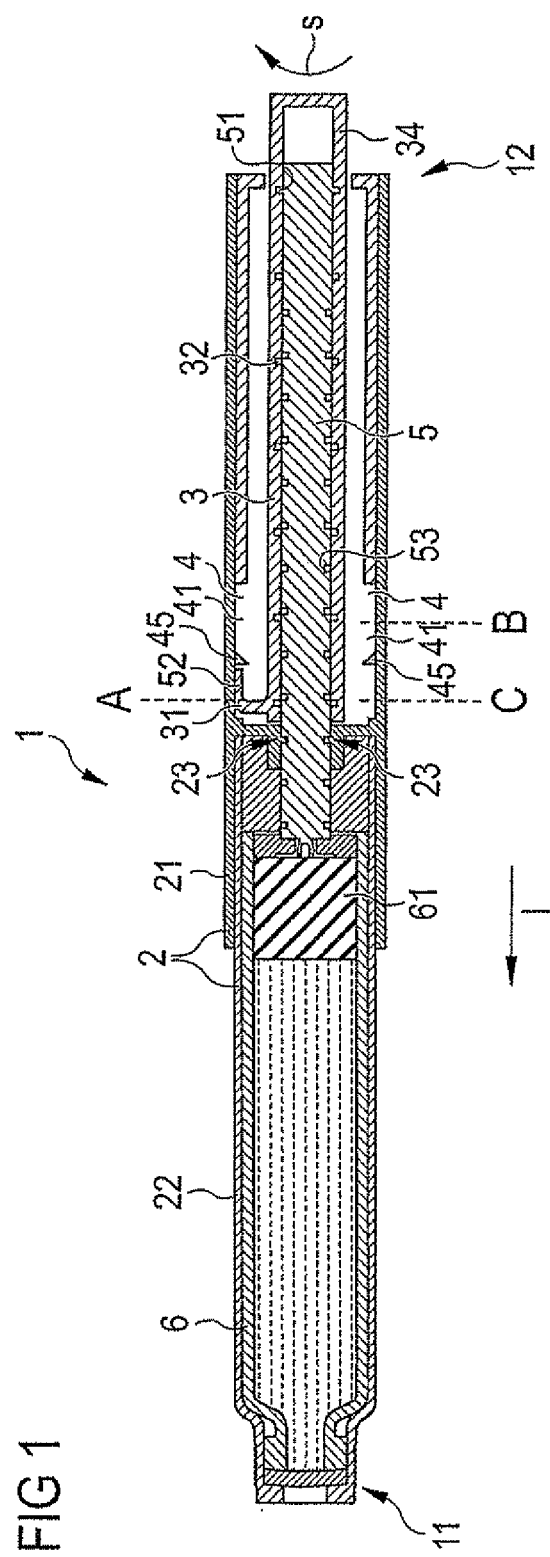

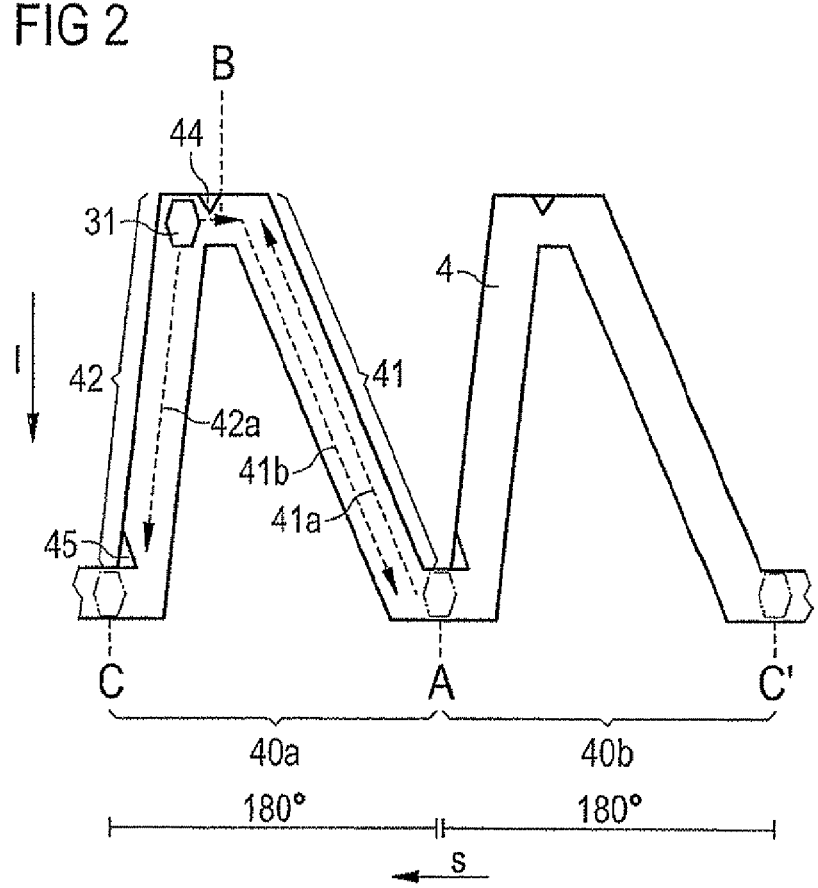
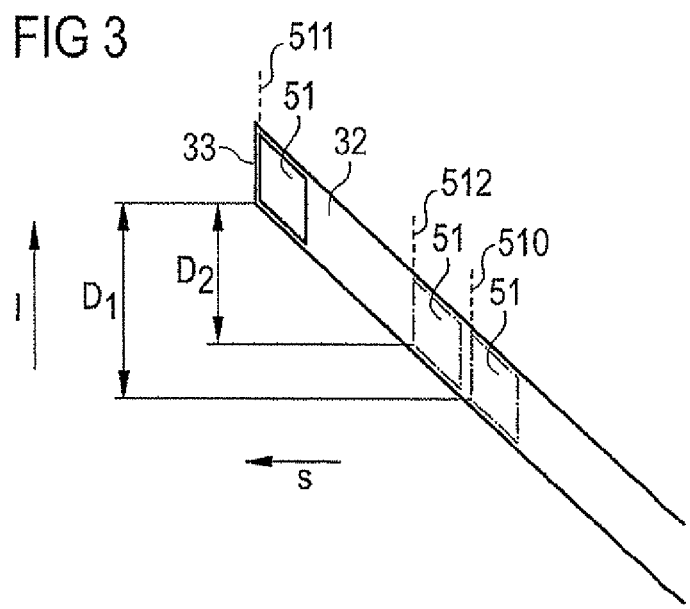

INJECTION DEVICE

CROSS REFERENCE TO RELATED APPLICATIONS

The present application is a U.S. National Phase Application pursuant to 35 U.S.C. §371 of International Application No. PCT/EP2009/067480 filed Dec. 18, 2009, which claims priority to EP Patent Application No. 08022317.5 filed on Dec. 23, 2008. The entire disclosure contents of these applications are herewith incorporated by reference into the present application.

FIELD OF THE INVENTION

This disclosure relates to an injection device for administering a fixed dose of a medication. In particular, it relates to a drive mechanism for such an injection device.

BACKGROUND

The patent application EP 1923084 A1 discloses an injection device for setting and dispensing a fixed dose of a medicament. Here, in order to set a dose, a user pulls a dose button in a proximal direction and, in order to dispense the dose, pushes the dose button towards a distal direction of the injection device.

The publication WO 2004/078239 A1 discloses an injection device, wherein a user can select the size of a dose. In order to set a dose, the user rotates a dose dial sleeve with respect to a housing and, in order to dispense dose, a user depresses a dose button.

SUMMARY

It is the aim of the present invention to provide an injection device for administering a fixed dose of a medication which is easy to use and highly reliable.

According to a first aspect of the present invention, an injection device for administering a fixed dose of a medication is provided. The injection device comprises a housing wherein a drive mechanism comprising a drive member is at least partially enclosed. Furthermore, the injection device comprises a dosing element which is permanently fixed relative to the drive member. A dose can be set by rotating the dosing element relative to the housing in a dose setting direction and the dose can be dispensed by pushing the dosing element towards the housing.

The drive member may be engaged with a piston rod acting on a piston in a cartridge wherein a medicament is disposed. Preferably, the movement of the dosing element and therewith the movement of the drive member towards the housing results in a movement of the piston rod towards the distal end of the injection device. Thereby, also the piston is moved forward and the medicament is pressed out of the cartridge.

Due to the fixed connection between the dosing element and the drive member, the user has direct control over the drive member. Thereby, a reliable setting and dispensing of the dose may be achieved, while further error-prone mechanical processes, e.g. a mechanical coupling or decoupling of the dosing element and the drive member, can be omitted. In addition to that, additional components can be saved and a cheaper production of the injection device may be achieved.

In a preferred embodiment, the movement of the dosing element during dose setting is not only rotational, but comprises a helical movement of the dosing element and the drive member away from the housing. In such an embodiment, both a pulling force on the dosing element and a rotational force in the dose setting direction may result in the helical movement of the dosing element and, thus, in setting the dose. Thereby, also a user who is confused or not familiar with the injection device is able to set a dose just by acting on the dosing element without having to bear in mind if a rotational movement or a pulling movement of the dosing element is required.

In a preferred embodiment, in order to set a dose, the user acts on the dosing element and moves the dosing element from an initial position to a stop position relative to the housing. At the stop position, the dosing element can neither be pulled further out of the housing nor be rotated further in the dose setting direction. When the dose setting element has reached the stop position, the dose setting is completed. At the stop position, a user may push the dosing element towards the housing until an end position is reached, whereby during this movement the medicament is dispensed.

In a preferred embodiment, a set dose can be cancelled by rotating the dosing element in a direction opposite to the dose setting direction.

Here, the dose may be cancelled when the dose setting has been completed and the stop position has been reached. The dose may also be cancelled from a position of the dosing element between the initial position and the stop position. Preferably, in order to cancel the dose, the dosing element is rotated in a direction opposite to the dose setting direction until the initial position is reached again.

This functionality may be particularly useful for a user who is not familiar with the injection device and, e.g., is trained to operate the injection device. Here, medical staff may wish to demonstrate to the user how the pen operates by setting a dose and cancelling the dose several times without having to expel any medicament. Furthermore, this may also be useful when a user after having set the dose decides that he wants to take the dose some time later and therefore, wishes to deselect the dose. This can not be achieved in an injection device wherein the only action available to the user after the dose has been set is to depress the dose button to expel the dose.

The injection device may comprise an indicator to indicate the user the two options after the dose has been set, i.e. dispensing the dose by pushing the dosing element or cancelling the dose by rotating the dosing element backwards. The indicator may be printed on the drive member and visible through an aperture in the housing.

In one embodiment, the dosing element is an integral part of the drive member.

This may be useful to further reduce the costs of producing the injection pen, because here the dosing element and the drive member can be produced in the same production step. Furthermore, the injection pen may be more robust.

The dosing element may be formed by an end part of the drive member extending beyond the end of the housing, such that it can be gripped by a user. In order to improve the handling of the dosing element, the dosing element may be provided with a grip surface or may have a cross-section larger than the cross-section of the drive member.

In an alternative embodiment, the dosing element may be a separate component which is permanently fixed relative to the drive member. This may be useful if a standard drive member is used in the injection device which cannot be conveniently gripped by a user.

In a preferred embodiment, the housing is threadedly engaged with the drive member.

In one embodiment, the housing may have an inner thread which engages with an engaging feature of the drive member. Alternatively, the drive member may have an outer thread which engages with an engaging feature of the housing.

In the following, it is assumed that the drive member has an engaging feature which engages with an inner thread of the housing. However, the following description encloses also embodiments, wherein the drive sleeve comprises an outer thread engaging with an engaging feature of the housing.

When a user acts on the dosing element in order to set a dose or to dispense a dose, the engaging feature travels along the path of the thread. Preferably, the engaging feature is guided by the path of the thread such that a movement of the drive member relative to the housing has to be in compliance with the path of the thread. Here, the position of the dosing element relative to the housing may be defined by the position of the engaging feature relative to the associated thread. As the user has direct control over the drive member, he may directly control the relative movement of the engaging feature along the path of the thread. Thereby, the risk is reduced that the engaging feature locks in the thread, e.g., due to high levels of friction or contamination from debris entering the device.

In one embodiment, the housing has a longitudinal axis and the inner thread of the housing oscillates between two confining positions at the longitudinal axis.

Here, when following the path of the thread, the thread runs towards one of the confining positions and then changes its direction and runs towards the second confining position. Thus, along the longitudinal axis, the path of the thread is confined to a region between the two confining positions. The path of the thread may reach the confining positions or may change its direction before a confining position is reached.

The inner thread of the housing may comprise several consecutive identical segments, which are arranged one after another in a consecutive order.

Preferably, each segment corresponds to a process of dose setting and dose dispensing.

The drive member may comprise two or more engaging features each engaging with a different segment of the inner thread of the housing. The engaging features may be arranged at symmetric positions around a longitudinal axis. As an example, two diametrically opposite engaging features may be guided by one segment of the thread each. In this case, the engagement of the drive member with the housing may be more robust and the risk for disengagement or locking may be reduced.

In a preferred embodiment of the segments of the inner thread, each segment comprises a dose setting section being inclined against the longitudinal axis and a dose dispense section being less inclined against the longitudinal axis than the dose setting section.

Preferably, when the user in order to set a dose rotates the dosing element in the dose setting direction, the engaging feature travels along the dose setting section in the dose setting direction. The dose setting section may extend from a first position towards a second position which is further away from the distal end, thereby running helically around the longitudinal axis along the dose setting direction. Preferably, the first position corresponds to the initial position of the dosing element and the second position to the stop position of the dosing element.

Preferably, the dose dispense section starts at the end of the dose setting section and extends towards a third position, wherein the third position is located closer towards the distal end than the second position. In one embodiment, the third position is located at the same position relative to the longitudinal axis as the first position and has an angular offset relative to the first position. When a user pushes the dosing element towards the housing the engaging feature moves from the second position to the third position of the inner thread of the housing. Preferably, the inclination of the dose dispense section against the longitudinal axis is such that the dosing element carries out a mainly translational movement along the axis when the user pushes the dosing element.

In a preferred embodiment, the dose dispense section runs in a direction parallel to the longitudinal axis.

Here, the action of pushing the dosing element results in a mainly translational movement of the dosing element relative to the housing. This may be very convenient for the user as he does not feel a rotational movement of the dosing element when pushing the dosing element.

In other embodiments, the dose dispense section may run in a direction not purely parallel to the longitudinal axis. Thereby, the mechanical advantage of the movement of the dosing element and the movement of the piston inside the cartridge may be improved.

In a preferred embodiment, during cancelling a dose, the engaging feature of the drive member travels along the dose setting section in a direction opposite to the dose setting direction. Here, the dose setting section has the double function of setting and cancelling the dose. When a user during the setting of the dose or at the end of the setting process decides that he does not want to expel the dose, he may rotate the dosing element towards the opposite direction. Thereby, the engaging feature of the drive member travels along the dose setting section in a backward direction.

In a preferred embodiment, the injection device comprises a detent, which gives an audible or tactile signal when the dose setting has been completed.

The detent may be located at the inner thread of the housing and precede the dose dispense section in the dose setting direction. The detent may interact with the engaging feature of the drive member, whereby an audible or tactile signal is given. As an example, the detent may be an element fixed at the inner thread of the housing and extending into the path of the inner thread. The detent may comprise a flexible or unflexible protrusion. Additionally or alternatively, the engaging feature may comprise a flexible part. In a preferred embodiment, when the engaging feature is moved against the detent, the engaging feature may overcome the detent due to a flexible deformation of one or both of the detent and the engaging feature. The audible or tactile feedback may result from the mechanical resistance of the elements when pushed against each other or from the snapping back of one or both of the elements after the engaging feature has passed the detent.

In alternative embodiments, the detent may be positioned at a distance further away from the inner thread. Here, it may interact with a part of the drive member which extends from the engaging feature or a separate part of the drive member. The detent and the interacting element are located such that the interaction results in an audible or tactile feedback when the engaging feature reaches the dose dispense section.

In one embodiment, the injection device comprises a non-return feature which allows a movement of the engaging feature of the drive member along the dose setting section and prevents a backward movement along the dose dispense section.

The non-return feature may be located at the end of the dose dispense section. Similar to the detent feature, the non-return feature may be a protrusion extending into the path of the inner thread of the housing. It may have a lead in such that at the end of the dose dispense section, a further movement of the engaging feature in the same direction is supported. Coming from the other direction, the non-return feature may have a stop face, such that the movement of the engaging feature in the backward direction along the dose dispense section is prevented.

The non-return feature may also be located at the housing or at a position further away from the inner thread and may engage with a separate element of the drive member as long as the interaction takes place when the engaging feature has passed the dose dispense section.

In a preferred embodiment, the segment of the inner thread takes up an angular range of 60°, 72°, 90°, 120° or 180°.

Preferably, the angular range of a segment is chosen such that a dose setting and a dose dispensing movement of the dosing element can be conveniently carried out by a user. With an angular range of 180°, the user has to rotate the dosing element about half a turn and then has to push the dosing element.

In a preferred embodiment, the inner thread is closed in itself.

Here, preferably, the angular range of a segment is an integral fraction of 360°. In this case, the consecutive segments complete a full turn along the inner diameter of the housing and join up after the full turn.

In case that the dispensing of only a few doses of a medicament is required, the inner thread may be terminated at its end. Here, the inner thread may take up an angular range of less than 360°.

Preferably, a piston rod is provided, the piston rod acting on a piston disposed in a cartridge wherein the medicament is contained. In a preferred embodiment, the piston rod moves rotationally during dispensing the dose.

In one embodiment, the drive member is a drive sleeve which at least partially encloses a piston rod. The piston rod may be threadedly engaged with the drive member.

The drive sleeve may have an inner thread which engages with an engaging feature of the piston rod.

Alternatively, the drive sleeve may comprise an engaging feature engaging with an outer thread of the piston rod.

In the following, it is assumed that the drive sleeve has an inner thread which engages with an engaging feature of the piston rod. However, the following description encloses also embodiments, wherein the drive sleeve comprises an engaging feature engaging with an outer thread of the piston rod.

Preferably, the lead of the inner thread of the drive sleeve equals the lead of the dose setting section of the inner thread of the housing. Thereby, when the dosing element and the drive sleeve are helically moved out of the housing to set a dose, the inner thread of the drive sleeve carries out a helical movement relative to the piston rod, while the piston rod itself remains stationary relative to the housing. During dose setting, the drive member carries out a mainly translational movement relative to the housing in the direction towards the distal end. By the threaded engagement of the drive sleeve with the piston rod, the movement of the drive sleeve results in a movement of the piston rod.

The ratio of the amounts of movement along the longitudinal axis of the injection device of the drive member and the piston rod depends on the mechanical advantage of the device.

Preferably, the piston rod is threadedly engaged with the housing. In particular, the piston rod may be a double-threaded lead screw.

In a preferred embodiment, the inner thread of the drive sleeve comprises a stop face which prevents full setting of a dose after the last available dose has been dispensed.

Thereby, when a user tries to set a dose after the last available dose has been dispensed, the engaging feature of the piston rod may abut against the stop face of the inner thread of the drive sleeve. As the piston rod is engaged with the housing, a counterforce is exerted on the drive sleeve such that a further movement of the drive sleeve in the dose setting direction and the full setting of a further dose is prevented.

In a preferred embodiment, the injection device is a pen-type device. As an example, the cartridge may contain medicaments like heparin, GLP1 or insulin.

BRIEF DESCRIPTION OF THE FIGURES

Other features will become apparent from the following detailed description when considered in conjunction with the accompanying drawings.

FIG. 1 is a cross-sectional view of an injection device comprising a drive mechanism, FIG. 2 is an unwound depiction of the inner thread of the housing engaged with an engaging feature of the drive member, FIG. 3 is an unwound depiction of the inner thread of the drive member engaged with an engaging feature of the piston rod.

DETAILED DESCRIPTION

FIG. 1 shows a pen-type injection device 1 having a longitudinal axis 1. The injection device 1 comprises a housing 2 with a main part 21 and a cartridge holder 22 wherein a cartridge 6 containing a liquid medicament is disposed. A needle unit (not shown here) can be attached to the distal end 11 of the injection device 1. The main housing 21 partially encloses a drive mechanism comprising a drive member 3 in the form of a drive sleeve partially enclosing a piston rod 5. The piston rod 5 acts on a piston 61, whereby during a movement towards the distal end 11 the medicament is pressed out of the cartridge.

At the proximal end 12 of the injection device 1, the drive member 3 extends beyond the main housing 21 such that the dosing element 34 formed by the end of the drive member 3 can be gripped by a user. Thereby, a user may set, dispense or cancel a fixed dose of a medicament.

The drive member 3 is threadedly engaged with the housing 2. The main part of the housing 21 comprises an inner thread 4, wherein an engaging feature 31 of the drive member 3 is guided. The inner thread 31 of the main part of the housing 21 runs along a helical path around the longitudinal axis 1.

The piston rod 5 is threadedly engaged with the drive member 3. The drive member 3 comprises an inner thread 32 engaged with an engaging feature 51 of the piston rod 5. In addition to that, the piston rod 5 is threadedly engaged with the housing 2. For this aim, the piston rod 5 comprises an outer thread 53, wherein an engaging feature 23 of the housing 2 is guided. Thus, the piston rod 5 is a double-threaded lead screw.

In order to set a dose, a user grips the dosing element 34 and rotates the dosing element 34 in a dose setting directions, resulting in a helical movement of the dosing element 34 and the drive member 3 away from the housing 2. The position of the dosing element 34 and the drive member 3 relative to the housing 2 may be defined by the position of the engaging feature 31 of the drive member 3 relative to the inner thread 4 of the housing 2. Starting from an initial position A, the dosing element 34 moves helically towards a stop position B. Due to the design of the inner thread 4 of the housing 2 and the inner thread 32 of the drive member 3, during the setting of the dose, the piston rod 5 remains stationary relative to the housing 2.

At the stop position B, a user can dispense the dose by pushing the dosing element 34 towards the distal end 11 until an end position C is reached. During this movement of the dosing element 34 and the drive member 3, a force is exerted on the piston rod 5 by the threaded engagement of the piston rod 5 with the drive member 3 and the housing 2. Thus, the piston rod 5 moves helically towards the distal end 11 and pushes the piston 61 forward. Thereby, the medicament is pressed out of the cartridge 6. The mechanical advantage of the injection device 1 is defined by the ratio of the axial displacement of the drive member 3 to the axial displacement of the piston rod 5 during dispensing the dose. It depends on the ratio of the lead of the inner thread 32 of the drive member 3 to the lead of the outer thread 53 of the piston rod 5.

Instead of pushing the dosing element 34 from the stop position B to the end position C and thereby dispensing the dose, the user may also cancel the set dose by twisting the dosing element 34 in a direction opposite to the dose setting direction s. Also here, during cancelling the dose, the piston rod 5 remains stationary relative to the housing 2.

FIG. 2 shows the inner thread 4 of the housing 2, wherein the engaging feature 31 of the drive member 3 is engaged. The path of the inner thread 4 runs around the inside diameter of the housing 2. For an illustrative purpose it is shown rolled out flat here.

The inner thread 4 completes a full turn such that the positions C and C' coincide. The inner thread 4 comprises two consecutive identical segments 40*a* and 40*b* each taking up an angular range of 180°. Each segment 40*a*, 40*b* comprises a dose setting section 41 and a dose dispense section 42. During a setting of the dose, the engaging feature 31 of the drive member 3 travels along the dose setting section 41 from the initial position A towards the stop position B, and thereby moves helically around the longitudinal axis 1 of the injection device 1 in the dose setting direction s. The lead of the dose setting section 41 is equal to the lead of the inner thread 4 of the housing 2. Therefore, the piston rod 5 does not move relative to the housing 2 during the dose setting process. At the stop position B, the dose setting process is completed. A detent 44 is located at the stop position B which gives an audible or tactile signal when the engaging feature 31 passes the detent 44. The engaging feature 31 has a flexible part (not shown here) which flexes backwards when pushed against the detent. By the interaction of the detent 44 with the engaging feature 31, a user is informed that the dose has been set. Thereby, the user can decide if he wants to dispense the dose or cancel the set dose.

For dispensing the dose, at the stop position B, the user pushes the dosing element 34 towards the distal end 11 of the injection device 1. Thereby, the engaging feature 31 follows the path of the dose dispense section 42 until it reaches the end position C. By this movement, the piston rod 5 is also moved towards the longitudinal direction and thereby, a medicament is pressed out of the cartridge 6. In this embodiment, the dose dispense section 42 runs in a direction not purely parallel to the longitudinal axes 1. At the end of the dose dispense section 42, a non-return feature 45 is located. The engaging feature 31 can pass the detent feature 45 when moving from the stop position B towards the end position C. However, the engaging feature 41 cannot pass the non-return feature 45 when moving in the opposite direction.

At the position B, instead of pushing the dosing element 34 in order to dispense the dose, a user may cancel the dose by rotating the dosing element 34 in a direction opposite to the dose setting direction s. Thereby, the engaging feature 31 travels backwards along the path of the dose setting section 41 from the stop position B towards the initial position A. During this movement, the drive member 3 moves along a helical path towards the distal end 11 of the injection device 1, while the piston rod 5 remains stationary relative to the housing 2.

After a cycle of dose setting and dose dispensing has been carried out, a user may set and dispense a new dose, wherein the engaging feature 31 is now guided by the consecutive segment 40*b*. Thus, multiple fixed doses of a medicament may be dispensed.

In a further embodiment of the injection device 1, the drive member 3 may comprise two engaging features, wherein one of the engaging features travels in the segment 40*a* and the other one in the segment 40*b* during a dose setting and dose dispense cycle.

FIG. 3 shows an embodiment of the inner thread 32 of the drive member 3 guiding the engaging feature 51 of the piston rod 5. The path of the inner thread 32 runs along the inside diameter of the drive member 3. For an illustrative purpose, it is shown rolled out flat here.

The inner thread 32 of the drive member 3 comprises a stop face 33, which, after the last available dose has been dispensed, prevents the full setting of a further dose.

Before the last dose has been set, the engaging feature 51 of the piston rod 5 is located at the position 510 relative to the drive member 3. While the last dose is being set, the drive member 3 rotates out of the housing 2 on a helical path, while the piston rod 5 remains stationary relative to the housing 2. Thereby, relative to the inner thread 32 of the drive member 3, the engaging feature 51 of the piston rod 5 moves towards the position 511. In this position 511, the engaging feature 51 is adjacent to the stop face 33, but does not prevent the setting of the dose. When the dose is being dispensed, the piston rod 5 moves towards the distal end 11 of the injection device 1. After the dose has been dispensed, the engaging feature 51 of the piston rod 5 is located at the position 512 relative to the drive member 3. Due to the threaded engagement of the piston rod 5 with the drive member 3 and the housing 2, the axial displacement D1 of the piston rod 5 is smaller than the axial displacement D2 of the drive member 3.

If a user tries to set a subsequent dose, the drive member 3 can experience the axial displacement D2 relative to the piston rod 5 before the engaging feature 51 of the piston rod 5 abuts the stop face 33. This is insufficient to set a dose, because a full dose setting would require the axial displacement D1. Hence, the full dose can not be set. The ratio of the axial displacement D1 to that of the axial displacement D2 depends on the mechanical advantage of the injection device 1. In particular, where the drive member 3 moves axially relative to the housing 2 during dispense, the mechanical advantage is equal to the ratio D1/(D1-D2). Thus, for a mechanical advantage 3:1, the distance D2 is equal to two thirds of the setting distance D1 and for a mechanical advantage of 2:1, the distance D2 is equal to half of the setting distance D1.

The invention claimed is:

1. An injection device for administering a fixed dose of a medication comprising:

a housing directly engaged with a drive member having a dosing element permanently fixed thereto, is at least partially enclosed by the housing and has an inner surface; and a piston rod directly engaged with the inner surface of the drive member;

wherein the engagement between the housing and the drive member is through a combination of a thread and an engaging feature where each is located on one of the housing and the drive member, where the combination is configured to allow only a single predefined fixed dose to be set by rotating the dosing element and the drive member relative to the housing in a dose setting direction(s) such that the drive member moves axially in a proximal direction and the dose can be dispensed by pushing the dosing element in a distal direction towards the housing causing the drive member to directly move the piston rod distally, wherein the thread has a dose setting section with a first lead and a dose dispense section having a second lead that is different from the first lead, where the first lead allows rotation of the drive member without movement of the piston rod during dose setting and the second lead allows distal movement of the drive member causing simultaneous distal movement of the piston rod.

2. The injection device according to claim 1, wherein a set dose can be cancelled by rotating the dosing element in a direction opposite to the dose setting direction(s).

3. The injection device according to claim 1, wherein the dosing element is an integral part of the drive member.

4. The injection device according to claim 1, wherein the housing has an inner thread which engages with an engaging feature of the drive member.

5. The injection device according to claim 4, wherein the housing has a longitudinal axis and wherein the inner thread of the housing oscillates between two confining positions at the longitudinal axis.

6. The injection device according to claim 4, wherein the inner thread is closed in itself.

7. The injection device according to claim 4, wherein the inner thread is terminated.

8. The injection device according to claim 5, wherein along the dose setting direction(s) the inner thread of the housing comprises several consecutive identical segments.

9. The injection device according to claim 8, wherein the drive member comprises two or more engaging features each engaging with a different segment of the inner thread of the housing.

10. The injection device according to claim 8, wherein each segment of the inner thread comprises a dose setting section being inclined against the longitudinal axis and a dose dispense section being less inclined against the longitudinal axis than the dose setting section.

11. The injection device according to claim 8, wherein a segment takes up an angular range of 60°, 72°, 90°, 120° or 180°.

12. The injection device according to claim 10, wherein the dose dispense section runs in a direction parallel to the longitudinal axis.

13. The injection device according to claim 10, wherein during the setting of the dose the engaging feature of the drive member travels along the dose setting section in the dose setting direction(s).

14. The injection device according to claim 10, wherein during cancelling a dose the engaging feature of the drive member travels along the dose setting section in a direction opposite to the dose setting direction(s).

15. The injection device according to claim 10, comprising a non-return feature which allows a movement of the engaging feature of the drive member along the dose setting section and prevents a backward movement along the dose dispense section.

16. The injection device according to claim 1, wherein the drive member is a drive sleeve which at least partially encloses a piston rod and has an inner thread which engages with an engaging feature of the piston rod.

17. The injection device according to claim 16, wherein the piston rod is threadedly engaged with the housing.

18. The injection device according to claim 17, wherein the piston rod is a double-threaded lead screw.

19. The injection device according to claim 16, wherein the inner thread of the drive sleeve comprises a stop face which prevents the full setting of a dose after the last available dose has been dispensed.

20. The injection device according to claim 19, wherein during a further dose setting movement after the last available dose has been dispensed the engaging feature of the piston rod abuts against the stop face.

21. The injection device according to claim 1 being a pen-type device.

22. The injection device according to claim 1, wherein the piston rod acting on a piston disposed in a cartridge wherein the medicament is contained, and wherein during dispensing the dose the lateral movement of the piston rod differs from the lateral movement of the drive member.

23. The injection device according to claim 22 wherein during dispensing the dose the amount of lateral movement of the piston rod is smaller than the amount of lateral movement of the drive member.

24. The injection device according to claim 1, the piston rod acting on a piston disposed in a cartridge wherein the medicament is contained, and wherein during dispensing the dose the piston rod moves rotationally.

25. The injection device according to claim 1 where a detent is positioned in the thread between the dose setting section and the dose dispense section and is configured to generate a signal that the single predefined fixed dose has been set.

26. A method of operating an injection device for the administration of a fixed dose of a medication comprising the steps:
  A) setting only one predefined fixed dose by rotating a dosing element relative to a housing of the injection device in a dose setting direction following a single predefined path having a first lead that is directly proportional to the only one possible single predefined dose,
  B) pushing the dosing element towards the housing in a predefined path having a second lead that is different from the first lead; and
  C) rotating the dosing element during or at the end of step A) in a direction opposite to the dose setting direction to cancel the dose.

* * * * *